US006673018B2

United States Patent
Friedman

(10) Patent No.: US 6,673,018 B2
(45) Date of Patent: Jan. 6, 2004

(54) ULTRASONIC MONITORING SYSTEM AND METHOD

(75) Inventor: Zvi M. Friedman, Kiriat Bialik (IL)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 0 days.

(21) Appl. No.: 10/064,290

(22) Filed: Jun. 28, 2002

(65) Prior Publication Data

US 2003/0045796 A1 Mar. 6, 2003

Related U.S. Application Data

(60) Provisional application No. 60/316,445, filed on Aug. 31, 2001.

(51) Int. Cl.[7] .................................................. A61B 8/00
(52) U.S. Cl. ...................................................... 600/440
(58) Field of Search ................................. 600/437, 440, 600/441, 443, 447

(56) References Cited

U.S. PATENT DOCUMENTS

| | | | | |
|---|---|---|---|---|
| 4,274,422 A | * | 6/1981 | Anderson et al. | 73/625 |
| 4,703,356 A | * | 10/1987 | Herzog et al. | 358/160 |
| 4,843,483 A | * | 6/1989 | Bogner | 358/335 |
| 5,152,290 A | * | 10/1992 | Freeland | 600/443 |
| 5,622,174 A | * | 4/1997 | Yamazaki | 600/455 |
| 5,797,843 A | * | 8/1998 | Fitch et al. | 600/437 |
| 6,213,944 B1 | * | 4/2001 | Miller et al. | 600/437 |
| 6,540,680 B1 | * | 4/2003 | Kurosaki | 600/443 |

* cited by examiner

Primary Examiner—Francis J. Jaworski
(74) Attorney, Agent, or Firm—McAndrews, Held & Malloy, Ltd.; Peter J. Vogel; Michael A. Dellapenna

(57) ABSTRACT

Apparatus and methods for use in a diagnostic ultrasound system are disclosed. A display device has a first window for displaying live ultrasound images and a second window for displaying a reference cine image. The reference cine image is an image captured prior to the currently displayed live ultrasound images. The images of the first and second windows are synchronized by ECG gating. The apparatus and methods may be employed to image the heart, providing operators with a way to monitor the heart and detect subtle changes in heart condition from the time that a reference image was captured.

28 Claims, 3 Drawing Sheets

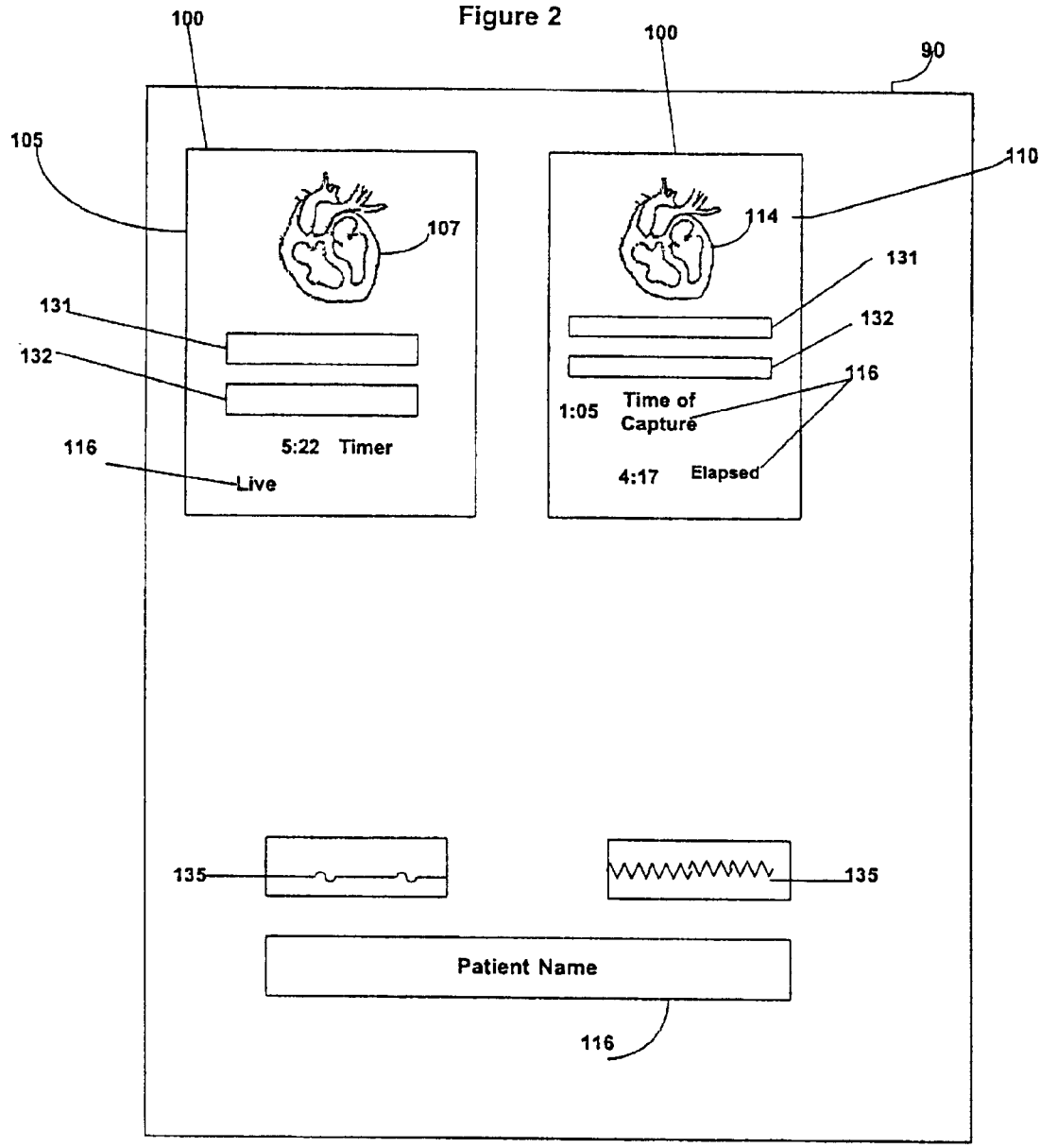

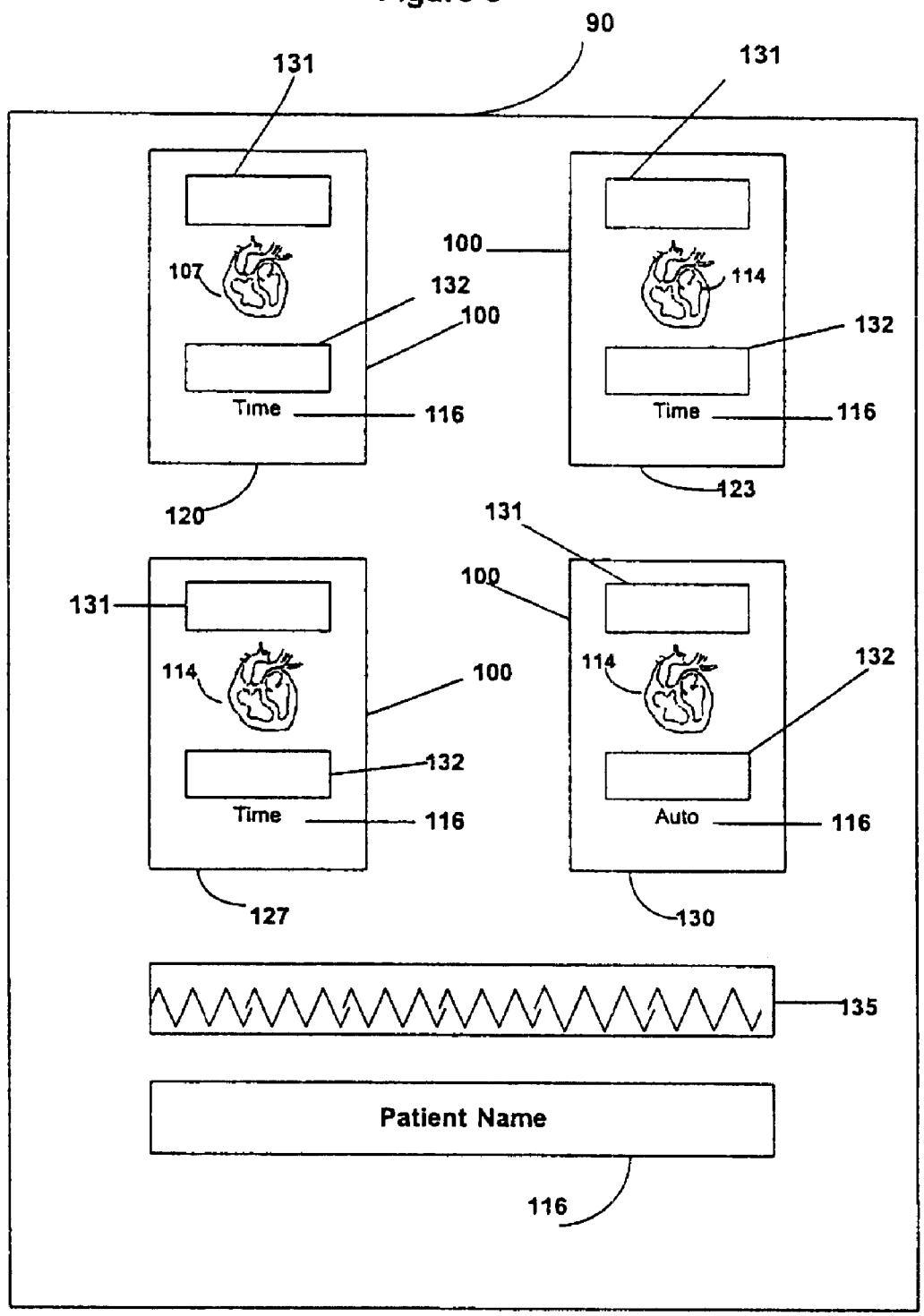

ULTRASONIC MONITORING SYSTEM AND METHOD

CROSS REFERENCE TO RELATED APPLICATIONS

This application claims the benefit of U.S. Provisional Application No. 60/316,445, filed Aug. 31, 2001.

BACKGROUND OF INVENTION

Certain embodiments of the present invention are directed generally to the field of diagnostic ultrasound imaging. More particularly, certain embodiments of the present invention are directed to the field of ultrasonic cardiac monitoring systems and methods.

When a patient is given anesthesia, there is a risk of myocardial infarction when the patient is in the induction phase or is in the phase of being awakened. One of the first signs of myocardial infarction is a change in left ventricular wall motion. Cardiologists, anesthesiologists, and other medical personnel have a need for early detection of signs of changes in left ventricular wall motion.

Conventional methods of monitoring patients' cardiac activity include watching the contraction of the left ventricle on an ultrasound diagnostic imaging system that obtains ultrasound data using a TEE probe lowered into the patient's esophagus. Employment of a TEE probe lowered into the patient's esophagus to monitor cardiac activity during surgery is potentially inaccurate because a physician has nothing to compare to the observed data and, therefore, the physician must memorize the previous functioning of the observed heart. Thus, if the difference between the current cardiac activity and previous cardiac activity is subtle, then the physician will not notice the change.

Another conventional method for monitoring cardiac activity involves using an ultrasound diagnostic imaging system to express general heart function using a single number representing the ejection fraction. The ejection fraction is the fractional change in the observed cross-sectional area of the left ventricle. Greater change in the cross-sectional area of the left ventricle over the cycle of a heartbeat indicates, better health of the heart. Physicians would like to observe changes in the single number representing ejection fraction because changes in that number may represent a significant change in the health of the heart. To obtain the number that represents ejection fraction, an algorithm is used to automatically trace the boundary of the endocardium by distinguishing between blood and heart tissue. Tracing is based on edge detection. Edge detection is performed by detecting sudden high video contrast between the heart muscle and the endocardium cavity, the former being displayed in shades of gray and the latter being displayed in black. Because tracing is based on edge detection, the operator may position a marker, using a track ball or other controller, in the left ventricle prior to tracing. Once the marker is positioned, the endocardium is automatically traced, identifying the inner border of the left ventricle. Tracing, however, may be lost from time to time if the image of the left ventricle is not of high quality because tracing will stop if the algorithm fails to detect the boundary between the endocardium cavity and heart tissue. Also, in some circumstances, tracing is not robust enough for obtaining an accurate number. When tracing is not very robust, tracing has too little contrast to obtain an accurate number to represent the ejection fraction.

Rather than using a TEE probe or edge detection to detect left ventricle motion, a Doppler method has also been employed to calculate cardiac output. Cardiac output is the volume of the blood that is ejected per unit time from the left ventricle when the left ventricle contracts. Cardiac output can be considered the volume of blood passing through the aorta per unit time, typically expressed in terms of liters per minute. Cardiac output is related to ejection fraction and heart rate. The Doppler method of detecting left ventricle motion requires probe manipulation by an operator, which increases the potential for human error. Measurements made by Doppler are proportional to the cosine of the angle formed between the directional velocity of the flow of blood and the beam direction. Because the angle formed between the directional velocity of the flow of blood and the beam direction changes over time, there is inaccuracy in the Doppler measurements. Also, the cross-sectional area of the vessel being analyzed must be measured, because the volume of blood passing through the vessel equals the cross-sectional area of the vessel multiplied by the velocity. But the cross-section of the vessel changes over time, because the vessel is elastic. Also, the angle from which the vessel is measured changes, changing the measured cross-section of the vessel. For example, the vessel must be measured from an angle perpendicular to the longitudinal axis of the vessel if the measurement is to accurately represent the actual vessel cross-section. If the vessel is not measured from an angle perpendicular to the longitudinal axis of the vessel, then the measurement will be the cross-sectional area of an ellipse, which is greater than the actual cross-sectional area of the vessel. Thus, the use of ultrasound measurements to determine cardiac output is an ineffective method of detecting the subtle changes in left ventricular wall motion that may precede a myocardial infarction.

SUMMARY OF INVENTION

One embodiment of the present invention is an apparatus for displaying a plurality of images in a diagnostic ultrasound system. The apparatus may comprise a display device having a first window for displaying a live ultrasound image and a second window for displaying a reference cine image. The images displayed in the first and second windows are synchronized by ECG gating. The images may be cardiac images. The reference image makes it easy for an operator to compare the current condition of the heart or other imaged region with the condition of that region at the time the reference image was captured.

The reference image may be captured and re-captured automatically at predetermined intervals. Alternatively, the reference image may be captured when the operator elects to capture the image, in which case the reference cine image is repeated until the operator elects to capture a new reference image. The reference cine image may be continuously updated so that the reference cine image lags behind the live ultrasound image by a pre-determined amount of time.

Alternative embodiments include a plurality of windows for displaying reference images. Embodiments having a plurality of windows for displaying reference images permit an operator to have a plurality of reference views of an area of interest that is displayed as a live ultrasound image in the first window.

A method in accordance with one embodiment of the present invention comprises the steps of displaying a live ultrasound image, displaying a reference cine image, and synchronizing, by ECG gating, the live ultrasound image and the reference cine image. The live ultrasound image and the reference cine image may be images of the heart. In a further embodiment, the method comprises the additional step of displaying a second reference cine image, wherein a view of the heart displayed in the first reference cine image is different from a view of the heart displayed in the second reference cine image. The reference cine image or images may be captured manually or may be captured and re-captured at a pre-determined interval. Alternatively, the reference cine image or images may be continuously updated so that the reference cine image or images lag behind the live ultrasound image by a pre-determined amount of time.

BRIEF DESCRIPTION OF DRAWINGS

The foregoing summary, as well as the following detailed description of the preferred embodiments of the present invention, will be better understood when read in conjunction with the appended drawings. For the purpose of illustrating the preferred embodiments of the present invention, there is shown in the drawings, embodiments which are presently preferred. It should be understood, however, that the present invention is not limited to the arrangements and instrumentality shown in the attached drawings.

FIG. 2 is a schematic diagram of a display system formed in accordance with one embodiment of the present invention.

FIG. 3 is a schematic diagram of a display system formed in accordance with an embodiment of the present invention.

DETAILED DESCRIPTION

Figure 1:
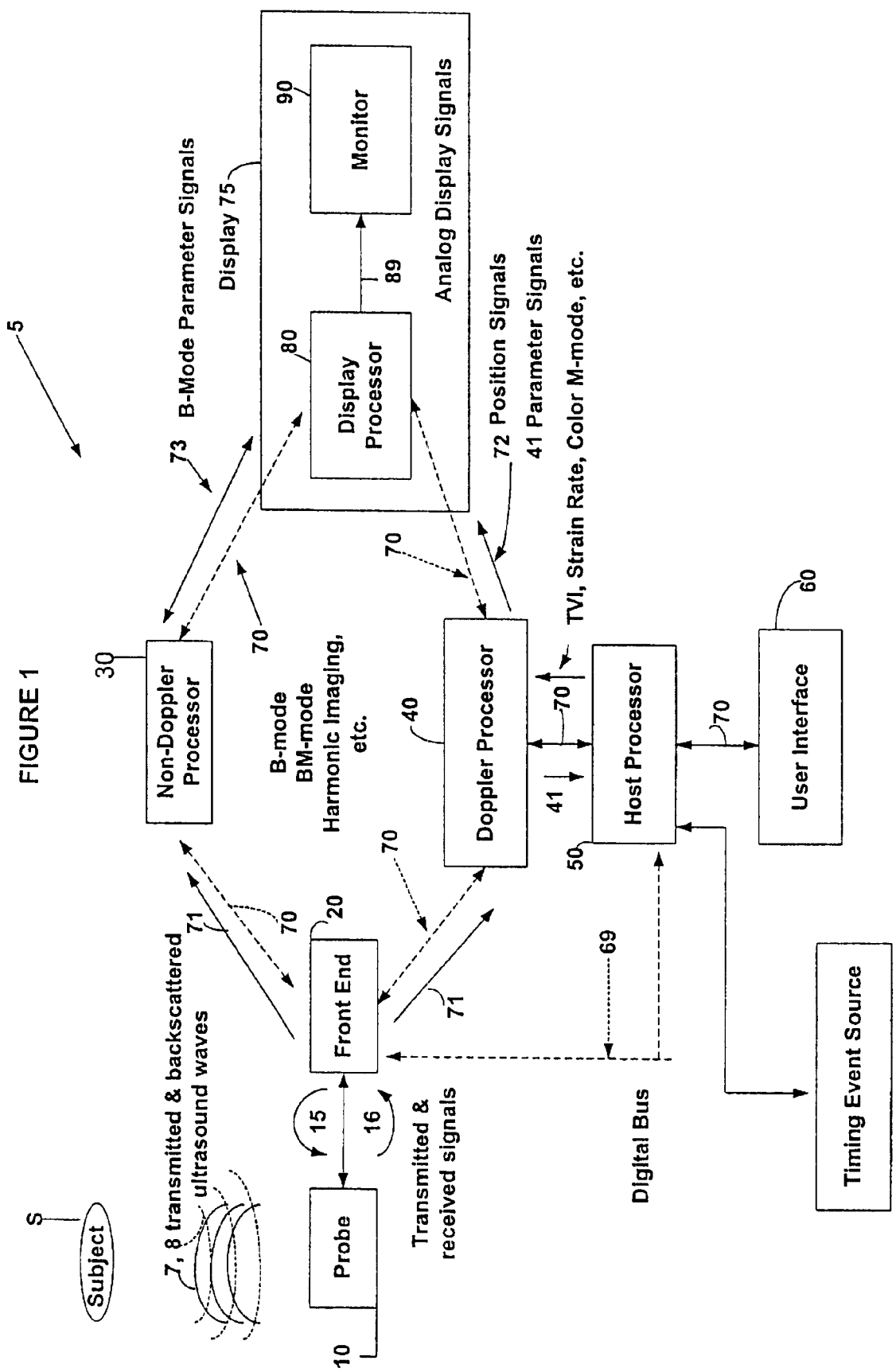
FIG. 1 is a block diagram of an ultrasound system formed in accordance with an embodiment of the present invention.

FIG. 1 is a schematic block diagram of a medical diagnostic ultrasound system 5. A probe 10 connected to the ultrasound system 5 is used to transmit ultrasound waves 7 into a subject S by converting electrical signals 15 into ultrasound energy. The probe 10 converts backscattered ultrasonic energy 8 to analog electrical signals 16. A front-end subsystem 20 comprising a receiver, transmitter, and beamformer is used to create transmitted waveforms, beam patterns and receiver filtering techniques that are used for various imaging modes. The front-end subsystem 20 interfaces at an analog interface to the probe 10 and interfaces at a digital interface over a digital bus 70 with a non-Doppler processor 30 and a Doppler processor 40 and interfaces over a digital bus 69 with a host processor 50. The digital buses 69 and 70 may comprise several digital sub-buses, each sub-bus having a unique configuration and providing digital data interfaces to various parts of the ultrasound system 5.

The non-Doppler processor 30 performs an amplitude detection function and data compression functions used for imaging modes such as B-mode, M-mode and harmonic imaging. The non-Doppler processor 30 and the Doppler processor 40 accept received signal digital data 71 from the front-end subsystem 20, process the signal digital data 71 into sets of signal values, and pass the signal values to the host processor 50 and/or a display 75 over the digital bus 69.

The display 75 includes a display processor 80 that performs a scan-conversion function, color mapping function, and tissue/flow arbitration functions based on the digital signals 41 and 73 from the non-Doppler processor 30 and the Doppler processor 40. Digital data 72, representing a location of a pattern of indicia, is accepted from host processor 50. The display processor 80 processes, maps, and formats the digital data 72 accepted from the host processor 50 for display, converts the digital display data to analog display signals 89, and passes these analog display signals 89 to a monitor 90. The monitor 90 accepts the analog display signals 89 from the display processor 80 and displays a resultant image 87 to the operator on the monitor 90.

A user interface 60 allows user commands to be input by the operator to the ultrasound system 5. The user interface 60 comprises a keyboard, mouse, switches, knobs, buttons, track ball, and on screen menus. The host processor 50 is the main, central processor of the ultrasound system 5. The ultrasound system 5 has been described as an example of an ultrasound system compatible with certain embodiments of the present invention. Embodiments of the present invention may be used in connection with ultrasound systems other than the ultrasound system S.

In FIG. 2 is shown an embodiment of the present invention comprising a display device, such as the monitor 90, having two windows 100. The display processor 80 (FIG. 1) has the capability of providing the monitor 90 with a plurality of windows 100. For example, in order to provide a plurality of windows 100, the display processor 80 may provide to the monitor 90 compound dynamic images produced by computer image manipulation. A first window 105 displays live ultrasound images 107. A second window 110 displays a reference cine image 114. The images 107, 114 may be images of the heart. The two windows 105, 110 are ECG gated to the ECG of the live ultrasound images 107 for synchronization.

The reference cine image 114 is an image captured earlier than the live images 107 currently being displayed. The reference cine image 114 may be captured at one time by the operator and then repeatedly displayed until the operator captures a reference image to replace it. Capture performed by an operator is called manual capture. With manual capture, the same cine image of a heart cycle, for example, keeps playing over and over while the live images 107 in the first window 105 are displayed until the operator captures a replacement reference cine image. The operator may perform capture, for example, by pressing a button on the user interface 60 (FIG. 1).

Alternatively, the second window 110 displays a reference cine image 114 that is automatically captured. An automatically captured image is a cine image that is updated or re-captured by the ultrasound system after a pre-determined amount of time passes. The operator may enter a number to indicate how much time must pass between updates of the reference image in the second window 110.

As seen in FIG. 2, an operator may annotate the windows with information 116. Annotations may include patient information. The window 100 that displays live images 107 may have a timer indicating how long that image 107 has been running. For example, the live image 107 of FIG. 2 has been running for five minutes and 22 seconds. The window 100 displaying a reference image 114 may have a number indicating the time at which the reference cine image 114 was captured, the time being the time that had been displayed with the live image 107 of the first window 105 when the reference image 114 was captured. For example, the reference image 114 in FIG. 2 was captured when the live image 107 had been running for one minute and five seconds. The reference image 114 of FIG. 2 has been running for four minutes and 17 seconds. If the reference image 114 is an automatic reference image, then the time of capture shown in that window 100 will be updated each time that the reference cine image 114 is updated (i.e., automatically captured). Additionally or alternatively, the time displayed in connection with either the manual or the automatic reference images 114 may be the time elapsed since the most recent capture (as noted above, an example of elapsed time of four minutes and 17 seconds is shown for the reference image 114 of FIG. 2). Although not shown in the Figures, for the automatic reference images 114, the pre-determined time between automatic captures may also be displayed.

In other embodiments the display screen may have more than two windows 100. For example, FIG. 3 shows an example of a display with four windows 100. A first window 120 displays live ultrasound images 107. Second and third windows 123, 127, respectively, may be manually captured reference images 114 of a cardiac cycle showing different views such as the long axis and short axis. A fourth window 130 may be an automatically captured reference cine image 114 of a cardiac cycle. All four windows 120, 123, 127, and 130 are ECG gated to the ECG of the live images 107 for synchronization. The windows shown in FIG. 3 may display annotations, capture times, elapsed times, and other times, as described in connection with the embodiment of FIG. 2. An annotation 131 describes the view of the displayed image in the window 100 in which the annotation 131 is located. For example, the annotation 131 may read "Long Axis" in a window 100 displaying a long axis view, and a different annotation 131 may read "Short Axis" in a window 100 displaying a short axis view. Other information may be included, additionally or alternatively, in the annotation 131, such as whether the image in the window 100 is a view of the heart during inhalation or whether the image is a view of the heart during exhalation. In FIG. 3, the annotation "Time" is not used to indicate a single particular type of time display but rather indicates that one or more of a variety of time display formats may be displayed. For example, an operator may select the desired time display, whether it be elapsed time, time of capture, or some other time display.

The reference images 114 allow an operator to readily compare the live image 107 of the heart with past images of the heart. Reference images 114 may be particularly helpful soon after a patient has been given a fluid or other treatment that affects heart function. An annotation 132 may be used to display the amount of time that has elapsed since administration of anesthesia was initiated. With the reference image or images 114, operators can determine whether the wall of the heart has moved after the treatment or whether other subtle changes may have occurred. Reference images 114 and live images 107 may be employed to monitor areas of the human body other than the heart, however, ECG triggering would still be employed to synchronize such images 114 and 107.

The positions of the live images 107 and the one or more reference images 114 may be determined by the operator. Thus, although shown on the left in FIG. 2, and in the upper left in FIG. 3, the live ultrasound images 107 may be shown in a different window 100, and a reference cine image 114 may be displayed in the left window (or upper left window in the embodiment of FIG. 3).

Any window 100 that is not displaying the live ultrasound image 107 may display either a manual reference image 114 or an automatic reference image 114. Thus, although FIG. 3 displays two manually captured reference windows 114 and one automatically captured reference window 114, embodiments of the present invention may have any combination of manually captured and automatically captured reference windows 114. Thus, an embodiment with a total of four windows 100 may comprise three manually captured reference windows 114, or three automatically captured reference windows 114, or other combinations of reference windows 114. The display device may also display data 135 such as a blood pressure graph, an ECG graph, and a breathing monitor.

All images (live images 107 and reference cine images 114) may be stored to an archiving system for review postoperatively. With a large enough amount of memory, the automatic reference images 114 could be updated continuously so that the automatic reference images 114 remain behind (i.e., lag behind) the live image 107 by a pre-determined amount of time. As time would pass, the memory or buffer storing the cine image would be updated so that the displayed automatic reference image 114 would be continuously changed to correspond to what the live image 107 had been at the pre-determined time earlier. If an image buffer can hold cine images of a duration equal to the pre-determined amount of time that the automatic reference image 114 is supposed to lag behind the live image 107, then the image buffer would be able to update the automatic reference images 114 continuously. If there is not enough memory to make such adjustments (or updates) to the automatic reference cine images 114, then the automatic reference cine images 114 will simply repeat until the pre-selected time has elapsed and a new reference cine image 114 is automatically captured. The pre-selected time may be determined by the operator.

Memory for storing the live and reference images 107, 114, respectively, may be provided by a computer. Images may be compressed to save memory, if desired. To conserve memory usage, images may be gated to only the contractility portion of the heart cycle. The windows 100 would then display only the contractility portion of the heart cycle which, for many applications, is the portion of the heart cycle of most interest to operators. The image 107 and reference image 114 data may be transmitted to remote locations over the Internet. Data compression techniques such as those mentioned above can facilitate transmission over the Internet.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A diagnostic ultrasound system comprising:
   an ultrasound probe;
   a processor for receiving data from said ultrasound probe to form display signals associated with a live ultrasound image and a reference cine image,
   an apparatus for displaying a plurality of images comprising:
      a single display device having a first window for displaying said live ultrasound image and a second window for displaying said reference cine image;
      wherein the images displayed in the first and second windows are synchronized by ECG gating to the ECG of said live ultrasound image.

2. The apparatus of claim 1, wherein the images displayed in the first and second windows are images of a heart.

3. The apparatus of claim 2, and comprising a third window:
   wherein the third window displays a reference cine image of the heart;
   wherein a view of the heart displayed in the second window is different from a view of the heart displayed in the third window; and wherein the images displayed in the first, second, and third windows are synchronized by ECG gating.

4. The apparatus of claim 1, wherein the reference cine image is captured manually.

5. The apparatus of claim 4, wherein the display device displays an amount of time that has elapsed since capture of the reference cine image.

6. The apparatus of claim 1, wherein the reference cine image is captured and recaptured at a pre-determined interval.

7. The apparatus of claim 6, wherein the display device displays at least one of an amount of time that has elapsed since capture of the reference cine image and an amount of time since initiating administration of anesthesia.

8. The apparatus of claim 1, wherein the display device has a window for displaying medical data.

9. The apparatus of claim 8, wherein the medical data displayed includes one of ECG data, blood pressure data, and a breathing monitor.

10. The apparatus of claim 1, and comprising a window for displaying annotations.

11. The apparatus of claim 1, and comprising third and fourth windows, wherein:
 the third and fourth windows display reference cine images;
 at least one of the reference cine images is captured and re-captured at a pre-determined interval;
 at least one of the reference cine images is captured manually; and
 the images displayed in the first, second, third, and fourth windows are synchronized by ECG gating and are images of a heart.

12. The apparatus of claim 1, wherein the reference cine image is continuously updated so that the reference cine image lags behind the live ultrasound image by a pre-determined amount of time.

13. In a diagnostic ultrasound system, an apparatus for displaying a plurality of images of the heart comprising:
 a single display device having a first window for displaying a live ultrasound image of the heart, a second window for displaying a reference cine image of a first view of the heart, and a third window for displaying a reference cine image of a second view of the heart;
 wherein the images displayed in the first, second, and third windows are synchronized by ECG gating.

14. In a diagnostic ultrasound system, an apparatus for displaying a plurality of images of the heart comprising:
 a single display device having a first window for displaying a live ultrasound image of the heart and a second window for displaying a reference cine image of the heart;
 wherein the images displayed in the first and second windows are synchronized by ECG gating;
 wherein the reference cine image is captured and re-captured at a predetermined interval; and
 wherein the display device displays at least one of an amount of time that has elapsed since capture of the reference cine image and an amount of time that has elapsed since initiating administration of anesthesia.

15. In a diagnostic ultrasound system, an apparatus for displaying a plurality of images of the heart comprising:
 a single display device having a first window for displaying a live ultrasound image of the heart, a second window for displaying a reference cine image of a first view of the heart, and a third window for displaying a reference cine image of a second view of the heart;
 wherein the images displayed in the first, second, and third windows are synchronized by ECG gating; and
 wherein at least one of the reference cine images is continuously updated so that the at least one reference cine image lags behind the live ultrasound image by a pre-determined amount of time.

16. A method for displaying a plurality of images in a diagnostic ultrasound system, the method comprising:
 displaying a live ultrasound image on a monitor;
 simultaneously displaying a reference cine image on the monitor; and
 synchronizing, by ECG gating, the live ultrasound image and the reference cine image.

17. The method of claim 16, wherein the live ultrasound image and the reference cine image are images of the heart.

18. The method of claim 17, and comprising the step of:
 displaying a second reference cine image;
 wherein a view of the heart displayed in the first reference cine image is different from a view of the heart displayed in the second reference cine image.

19. The method of claim 17, and comprising the step of capturing the reference cine image manually.

20. The method of claim 17, and comprising the step of capturing and re-capturing the reference cine image at a pre-determined interval.

21. The method of claim 16, and comprising the step of displaying at least one of an amount of time that has elapsed since capture of the reference image and an amount of time that has elapsed since initiating administering anesthesia.

22. The method of claim 16, and comprising the step of displaying medical data, wherein the medical data includes one of ECG data, blood pressure data, and a breathing monitor.

23. The method of claim 16, and comprising the step of continuously updating the reference cine image so that the reference cine image lags behind the live ultrasound image by a pre-determined amount of time.

24. The method of claim 16, and comprising the steps of:
 displaying second and third reference cine images;
 capturing at least one of the reference cine images manually; and
 capturing and re-capturing at least one of the reference cine images at a pre-determined interval.

25. The method of claim 16, and comprising the step of displaying annotations.

26. A method for displaying a plurality of images of the heart in a diagnostic ultrasound system, the method comprising:
 displaying a live ultrasound image of the heart on a monitor;
 simultaneously displaying a first reference cine image of the heart on the monitor;
 simultaneously displaying a second reference cine image of the heart on the monitor; and
 synchronizing, by ECG gating, the live ultrasound image and the first and second reference cine images;
 wherein a view of the heart displayed in the first reference cine image is different from a view of the heart displayed in the second reference cine image.

27. A method for displaying a plurality of images of the heart in a diagnostic ultrasound system, the method comprising:

displaying a live ultrasound image of the heart on a monitor;

capturing and re-capturing a reference cine image of the heart at a predetermined interval;

simultaneously displaying the reference cine image of the heart on the monitor;

displaying an amount of time that has elapsed since capture of the reference cine image; and synchronizing, by ECG gating, the live ultrasound image and the reference cine image.

28. A method, for displaying a plurality of images of the heart in a diagnostic ultrasound system, the method comprising:

displaying a live ultrasound image of the heart on a monitor;

simultaneously displaying a first reference cine image of the heart on the monitor;

simultaneously displaying a second reference cine image of the heart on the monitor, wherein a view of the heart displayed in the first reference cine image is different from a view of the heart displayed in the second reference cine image;

synchronizing, by ECG gating, the live ultrasound image and the first and second reference cine images; and continuously updating at least one of the first and second reference cine images so that the at least one reference cine image lags behind the live ultrasound image by a pre-determined amount of time.

* * * * *